(12) United States Patent
Oribe et al.

(10) Patent No.: US 7,909,835 B2
(45) Date of Patent: Mar. 22, 2011

(54) AUXILIARY INSTRUMENT FOR FIXING ROD

(75) Inventors: Kazuya Oribe, Tokyo (JP); Hiroshi Takamido, Nagoya (JP)

(73) Assignee: Showa IKA Kohgyo Co., Ltd., Aichi-Ken (JP)

( * ) Notice: Subject to any disclaimer, the term of this patent is extended or adjusted under 35 U.S.C. 154(b) by 854 days.

(21) Appl. No.: 11/073,590

(22) Filed: Mar. 8, 2005

(65) Prior Publication Data

US 2005/0261702 A1 Nov. 24, 2005

(30) Foreign Application Priority Data

Mar. 9, 2004 (JP) ................. P2004-066311

(51) Int. Cl.
*A61B 17/58* (2006.01)
(52) U.S. Cl. ...................... 606/104; 606/86 A
(58) Field of Classification Search .............. 606/246, 606/264, 279, 86 A, 86 R, 99, 104, 207, 72, 606/53, 54, 100, 205–208, 210, 211; 81/3.6, 81/3.7, 300, 304, 321, 342, 345, 350, 378, 81/420, 485; 7/125, 126
See application file for complete search history.

(56) References Cited

U.S. PATENT DOCUMENTS

| | | | | |
|---|---|---|---|---|
| 3,828,791 | A * | 8/1974 | Santos | 606/207 |
| 5,318,589 | A * | 6/1994 | Lichtman | 606/205 |
| 5,466,243 | A * | 11/1995 | Schmieding et al. | 606/232 |
| 5,578,032 | A * | 11/1996 | Lalonde | 606/54 |
| 6,440,133 | B1 | 8/2002 | Beale et al. | |
| 6,648,888 | B1 | 11/2003 | Shluzas | |
| 6,660,006 | B2 | 12/2003 | Markworth et al. | |
| 6,790,209 | B2 | 9/2004 | Beale et al. | |
| 2002/0020255 | A1 | 2/2002 | Simon et al. | |
| 2002/0040223 | A1 | 4/2002 | Sato et al. | |
| 2003/0009168 | A1* | 1/2003 | Beale et al. | 606/61 |
| 2003/0199872 | A1 | 10/2003 | Markworth et al. | |
| 2004/0049191 | A1 | 3/2004 | Markworth et al. | |
| 2005/0033299 | A1 | 2/2005 | Shluzas | |

FOREIGN PATENT DOCUMENTS

| | | |
|---|---|---|
| DE | 4238339 | 5/1994 |
| WO | 03/003928 | 1/2003 |
| WO | 03/088856 | 10/2003 |

OTHER PUBLICATIONS

English language Abstract of DE 4238339.

* cited by examiner

*Primary Examiner* — Eduardo C Robert
*Assistant Examiner* — Tara R Carter
(74) *Attorney, Agent, or Firm* — Greenblum & Bernstein, P.L.C.

(57) ABSTRACT

An auxiliary instrument for fixing a rod places a detent pin on a head portion of the screw. The auxiliary instrument comprises an inner cylinder, an outer cylinder, a first lever and a second lever. The inner cylinder has a plurality of claw portions and an opening employed to introduce the detent pin into an interior thereof. The outer cylinder is arranged to surround the inner cylinder and has a claw pressing portion. The first lever is rotatably connected to the inner cylinder and arranged in substantially perpendicular to an axial direction of the inner cylinder. The second lever is rotatably connected to the fist lever and the outer cylinder and arranged in substantially perpendicular to an axial direction of the outer cylinder. When the first and second levers are operated, the claw portions are pressed inward by the claw pressing portion to hold the head portion of the screw.

20 Claims, 10 Drawing Sheets

AUXILIARY INSTRUMENT FOR FIXING ROD

CROSS REFERENCE TO RELATED APPLICATION

This application claims benefit of priority under 35 U.S.C. §119 to Japanese Patent Application No. 2004-66311, filed on Mar. 9, 2004, the entire contents of which are incorporated by reference herein.

BACKGROUND OF THE INVENTION

1. Field of the Invention

The present invention relates to an auxiliary instrument for fixing a rod, which connects bones such as thoracic vertebrae or lumbar vertebrae, in engaging grooves which each is formed on a head portion of an implant (a screw) screwed into the bone.

2. Description of the Related Art

In a conventional bone connector, as shown in FIGS. 1 and 2, a vertebral body 101 is integrally connected to an adjacent vertebral body 101 by screwing implants (screws) 103 into the vertebral bodies 101 and then fixing a rod 105 to head portions of the screws 103.

A work for fixing the rod 105 to each of the screws 103 will be described in detail below. Firstly, the rod 105 passes through an engaging groove 107 formed on the head portion of the screw 103. Secondly, a detent pin 111 is placed on an upper surface of the engaging groove 107. Finally, the detent pin 111 is screwed into the engaging groove 107 by means of a tool for rotating the detent pin 111. Here, a male thread portion and a female thread portion are formed on an outer surface of the detent pin 111 and an upper part of an inner surface of the engaging groove 107, respectively.

In the above fixing work, if the detent pin 111 wobbles, it becomes harder to screw the detent pin 111 into the engaging groove 107. Further, if the detent pin 111 is dropped from the engaging groove 107, it is possible to hurt an incision part of a patient.

SUMMARY OF THE INVENTION

An object of the present invention is to provide an auxiliary instrument for fixing a rod capable of easily and stably screwing a detent pin into an engaging groove when the rod is fixed to an implant.

In order to achieve the above object, the present invention provides an auxiliary instrument for fixing a rod, the auxiliary instrument placing a detent pin employed to fix the rod to a screw on a head portion of the screw comprising: an inner cylinder having a plurality of claw portions at a first end portion thereof and an opening employed to introduce the detent pin into an interior thereof at a second end portion thereof; an outer cylinder arranged to surround the inner cylinder and having a claw pressing portion at a first end portion thereof; a first lever rotatably connected to the second end portion of the inner cylinder and arranged in substantially perpendicular to an axial direction of the inner cylinder; and a second lever rotatably connected to the first lever and a second end portion of the outer cylinder and arranged in substantially perpendicular to an axial direction of the outer cylinder, wherein the claw portions are pressed inward by the claw pressing portion to hold the head portion of the screw when the first lever and the second lever are operated.

According to the present invention, the auxiliary instrument prevents the detent pin from wobbling because the inner cylinder accommodates the detent pin at a time of screwing the detent screw into an engaging groove formed on the head portion of the screw. It therefore becomes easier to screw the detent pin into the engaging groove. The auxiliary instrument further prevents the detent pin from falling from the engaging groove because the inner cylinder accommodates the detent pin at the time of screwing the detent pin into the engaging groove. It is therefore not possible to hurt an incision part of a patient.

DESCRIPTION OF THE PREFERRED EMBODIMENT

First Embodiment

A bone connector 1 comprises implants (screws) 3, a rod 5 and a detent pin (not shown). An engaging groove (not shown) is formed on a square head portion of the screw 3. The rod 5 passes through a lower portion of the engaging groove.

Figure 1:
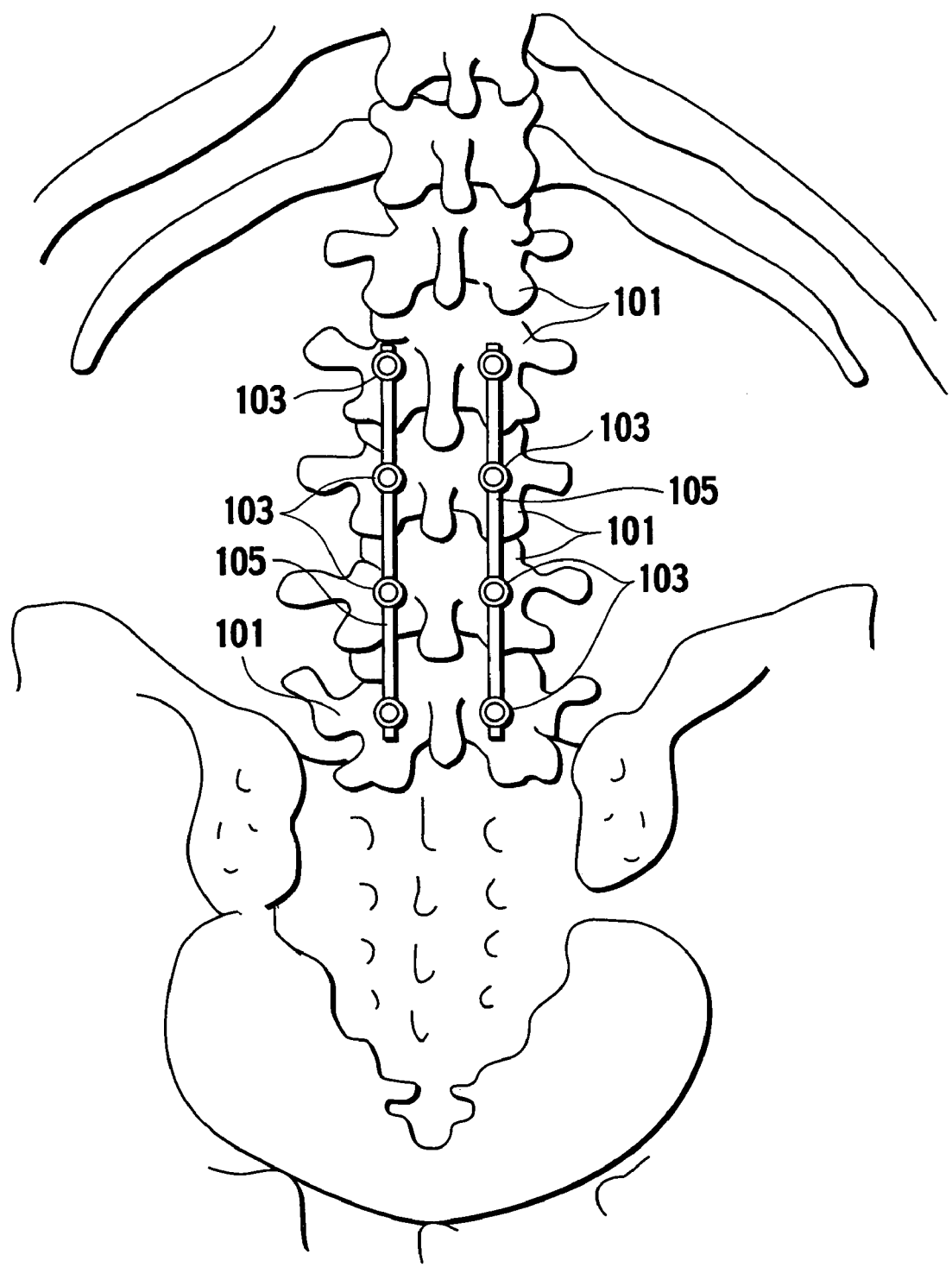
FIG. 1 is a plan view of a conventional bone connector in a state of fixing a rod to a screw.
Figure 2:
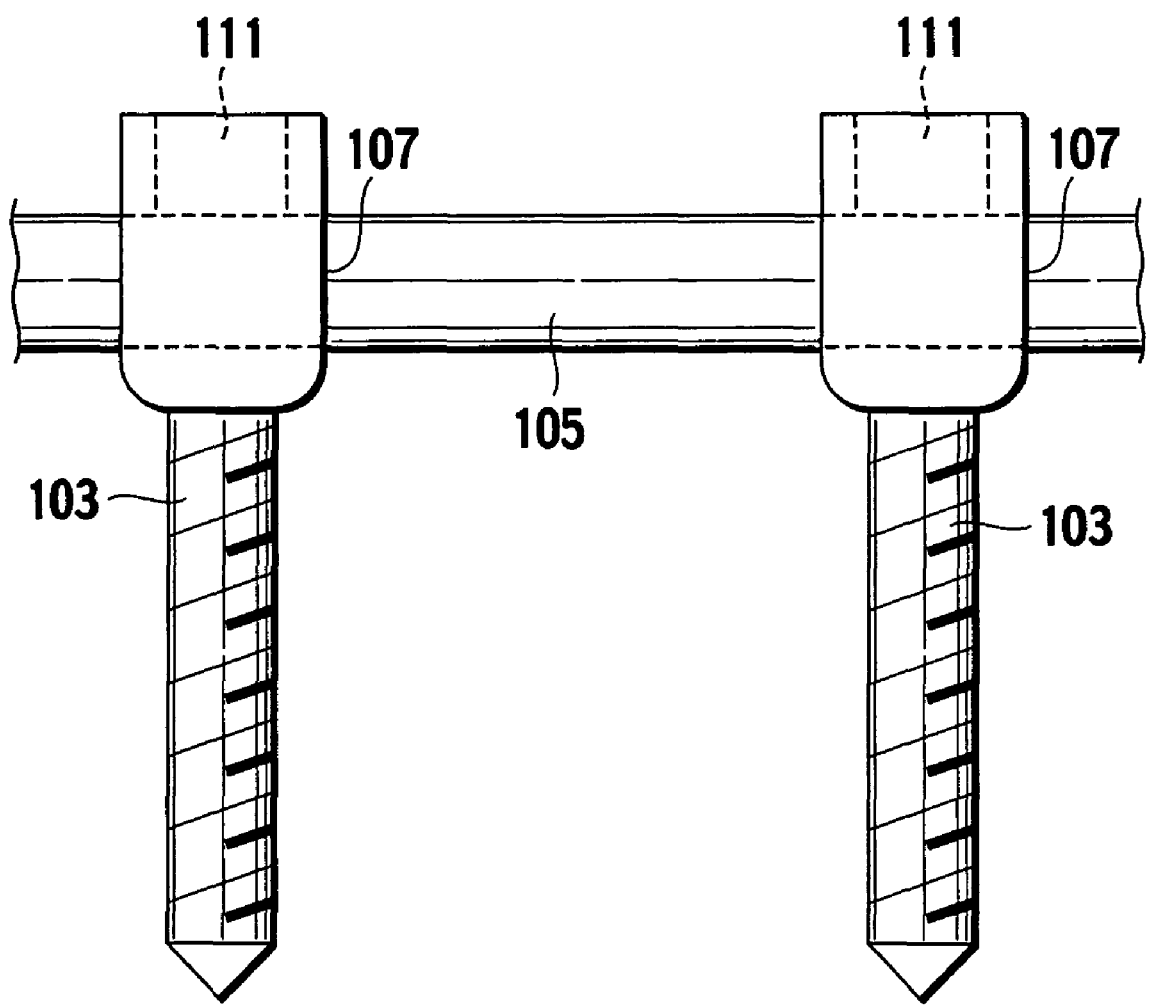
FIG. 2 is a side view of the conventional bone connector in the state of fixing the rod to the screw.
Figure 3:
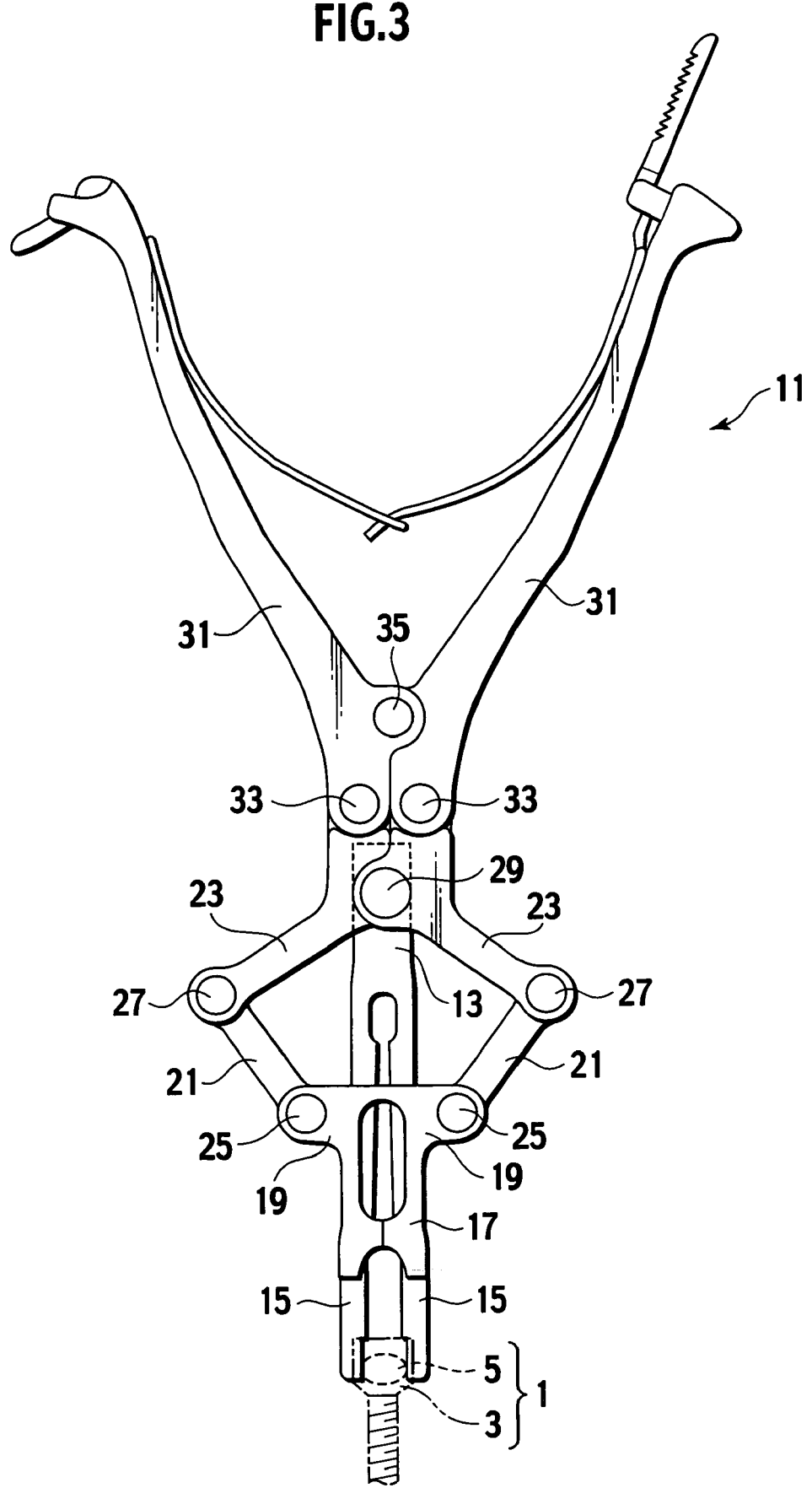
FIG. 3 is a front view of an auxiliary instrument for fixing a rod according to a first embodiment of the present invention.
Figure 4:
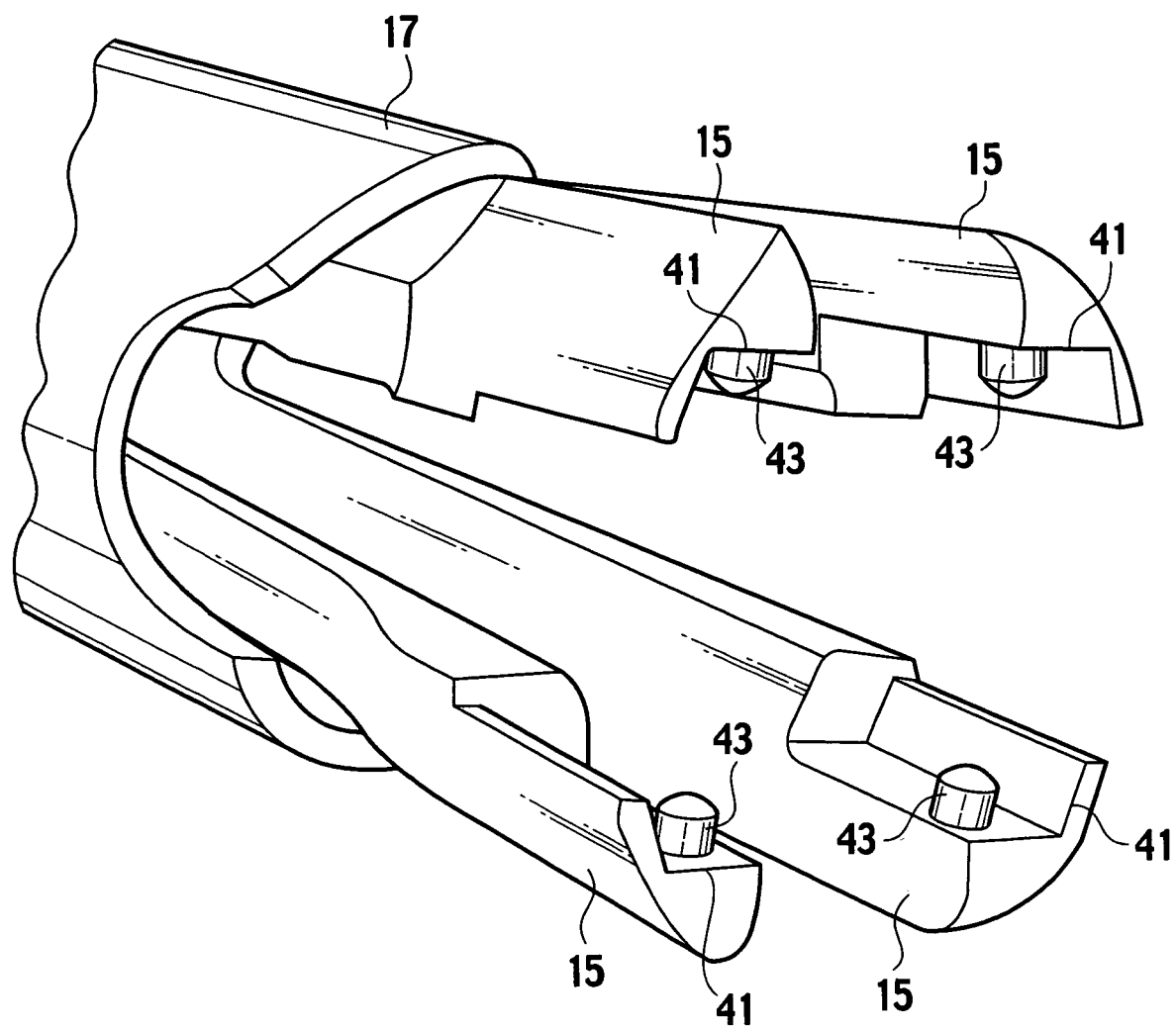
FIG. 4 is an enlarged perspective view of a lower portion of the auxiliary instrument for fixing a rod according to the first embodiment of the present invention.

As shown in FIGS. 3 and 4, an auxiliary instrument for fixing a rod 11 comprises an inner cylinder 13, claw portions 15, 15, 15, 15, an outer cylinder 17, brackets 19, 19, first links 21, 21, second links 23, 23, first hinge pins 25, 25, second hinge pins 27, 27, a first pivot 29, levers 31, 31, third hinge pins 33, 33 and a second pivot 35.

The inner cylinder 13 branches in four directions as gently inclining outward from the vicinity of a center portion thereof. The inner cylinder 13 further has the claw portions 15, 15, 15, 15 at distal ends of branch parts thereof (a lower end of the inner cylinder 13). The head portion of the screw 3 is sandwiched between the claw portions 15, 15, 15, 15. The outer cylinder 17 is arranged concentrically with the inner cylinder 13. The outer cylinder 17 further is able to move along an axial direction of the inner cylinder 13. If the outer cylinder 17 moves down relative to the inner cylinder 13, the claw portions 15, 15, 15, 15 approach one another as guided by an inner circumference surface of the outer cylinder 17. The brackets 19, 19 are mounted symmetrically on both sides of an upper portion of the outer cylinder 17. The brackets 19, 19 are extended from the outer cylinder 17 in a direction perpendicular to an axial direction of the rod 5.

The first links 21, 21 are rotatably linked to the brackets 19, 19 via the first hinge pins 25, 25 at first end portions thereof, respectively. The first links 21, 21 further are rotatably linked to first end portions of the bellcrank second links 23, 23 via the second hinge pins 27, 27 at second end portions thereof, respectively. The second links 23, 23 are rotatably linked to base end portions of the levers 31, 31 via the third hinge pins 33, 33 at second end portions thereof, respectively. The first hinge pins 25, 25, the second hinge pins 27, 27 and the third hinge pins 33, 33 are arranged in parallel to the axial direction of the rod 5.

The second links 23, 23 are connected each other via the first pivot 29 so as to be able to swing. The inner cylinder 13 is supported by means of the first pivot 29 at one end of the first pivot 29 via a bracket integrally mounted on an upper portion of the inner cylinder 13. The levers 31, 31 are connected each other via the second pivot 35 so as to be able to swing. Free end portions of the levers 31, 31 are extended so at to separate from each other.

Grooves 41, 41, 41, 41 are formed on inner surfaces of the claw portions 15, 15, 15, 15 so as to fit into shapes of four corners of the head portion of the screw 3. Engaging pins 43, 43, 43, 43 are provided in a protruding condition on inner surfaces of the grooves 41, 41, 41, 41. When the claw portions 15, 15, 15, 15 approach one another by moving the outer cylinder 17 down relative to the inner cylinder 13, the engaging pins 43, 43, 43, 43 are inserted into engaging holes (not shown) formed on the head portion of the screw 3.

A work for fixing the rod 5 to the screw 3 by means of the auxiliary instrument 11 will be described in detail below. Firstly, the rod 5 passes through the lower portion of the engaging groove formed on the head portion of the screw 3. Secondly, the four corners of the head portion of the screw 3 are inserted into the grooves 41, 41, 41, 41 of the auxiliary instrument 11. Thirdly, the engaging pins 43, 43, 43, 43 of the auxiliary instrument 11 are inserted into the engaging holes of the screw 3 by operating the levers 31, 31.

The operation of the levers 31, 31 will be described in detail below. An operator holds the levers 31, 31 in his/her one hand to bring the free end portions of the levers 31, 31 close to each other, which allows the base end portions of the levers 31, 31 to separate from each other. Thereby, the first end portions of the second links 23, 23 approach each other. The first links 21, 21 move the outer cylinder 17 down relative to the inner cylinder 13 via the brackets 19, 19, as the first end portions of the second links 23, 23 approach each other. When the outer cylinder 17 presses the claw portions 15, 15, 15, 15 inward via the inner circumference surface thereof, the claw portions 15, 15, 15, 15 approach one another. Thereby, the engaging pins 43, 43, 43, 43 of the auxiliary instrument 11 are inserted the engaging holes of the screw 3.

Fourthly, when the detent pin is dropped from an opening surface of the upper portion of the inner cylinder 13, the detent pin is guided by an inner circumference surface of the inner cylinder 13 and then placed on an upper surface of the engaging groove. Finally, a tool for rotating the detent pin is inserted from the opening surface of the upper portion of the inner cylinder 13 and a lower end portion of the tool is engaged to a tool engaging hole formed on an upper surface of the detent pin. Then, the detent pin is screwed into the engaging groove by rotating the tool.

Features of the auxiliary instrument 11 will be described below.

The auxiliary instrument 11 prevents the detent pin from wobbling because the inner cylinder 13 accommodates the detent pin at the time of screwing the detent pin into the engaging groove. Therefore, it becomes easier to screw the detent pin into the engaging groove.

The auxiliary instrument 11 prevents the detent pin from falling from the engaging groove because the inner cylinder 13 accommodates the detent pin at the time of screwing the detent pin into the engaging groove. Therefore, it is not possible to hurt an incision part of a patient.

Second Embodiment

Figure 8:
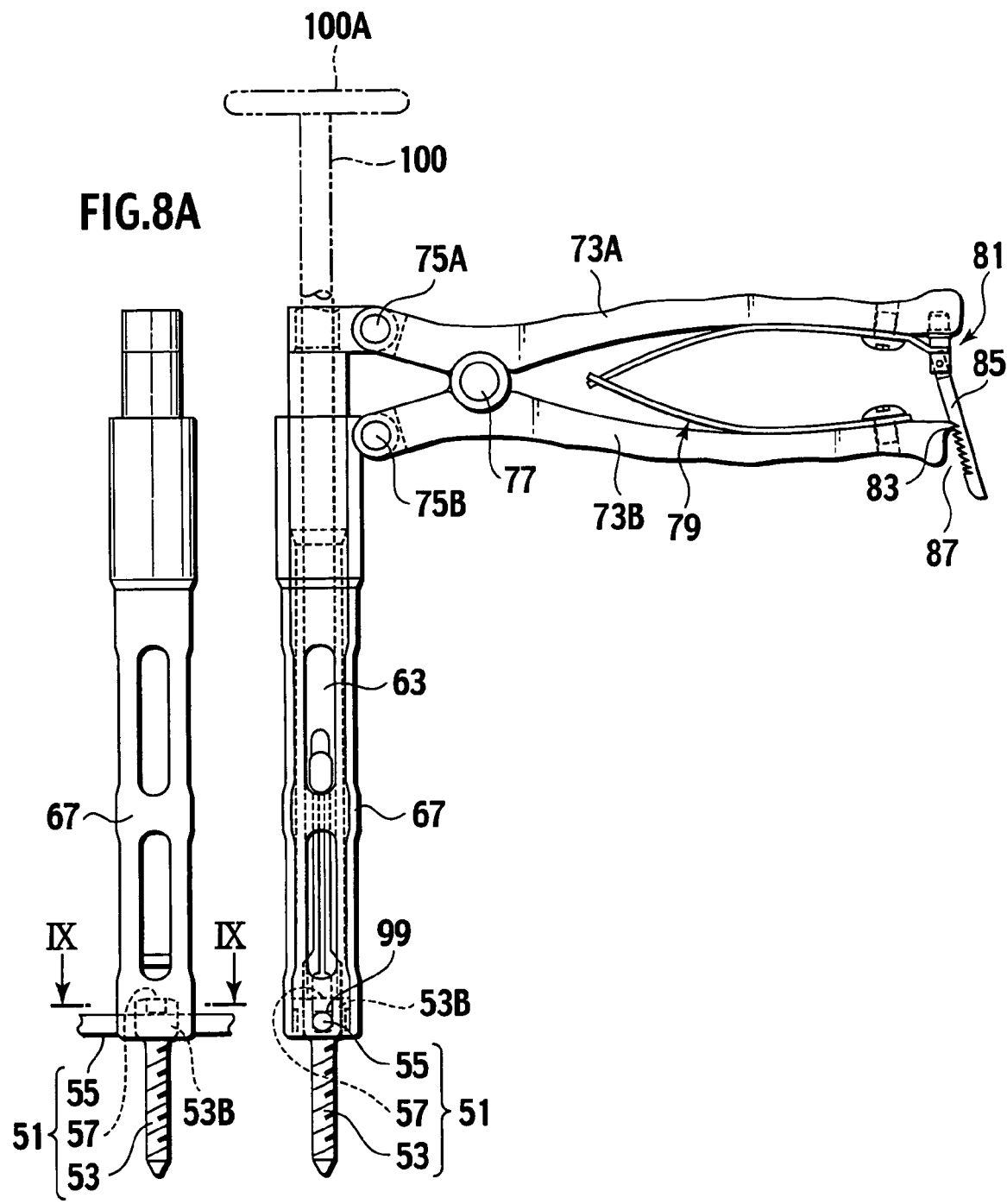
FIG. 8A is a side view of the auxiliary instrument for fixing a rod according to the second embodiment of the present invention, in a state of sandwiching a head portion of the screw between claw portions of the auxiliary instrument.
FIG. 8B is a front view of the auxiliary instrument for fixing a rod according to the second embodiment of the present invention, in a state of sandwiching the head portion of the screw between the claw portions of the auxiliary instrument and inserting a rotating tool into the auxiliary instrument.

A bone connector 51 comprises implants (screws) 53, a rod 55 and a detent pin 57 (see FIG. 8A). The screw 53 is screwed into a vertebral body such as a thoracic vertebra and a lumbar vertebra. The rod 55 connects a plurality of screws 53 one another. The detent pin 57 fixes the rod 55 to each of the screws 53.

Figure 5:
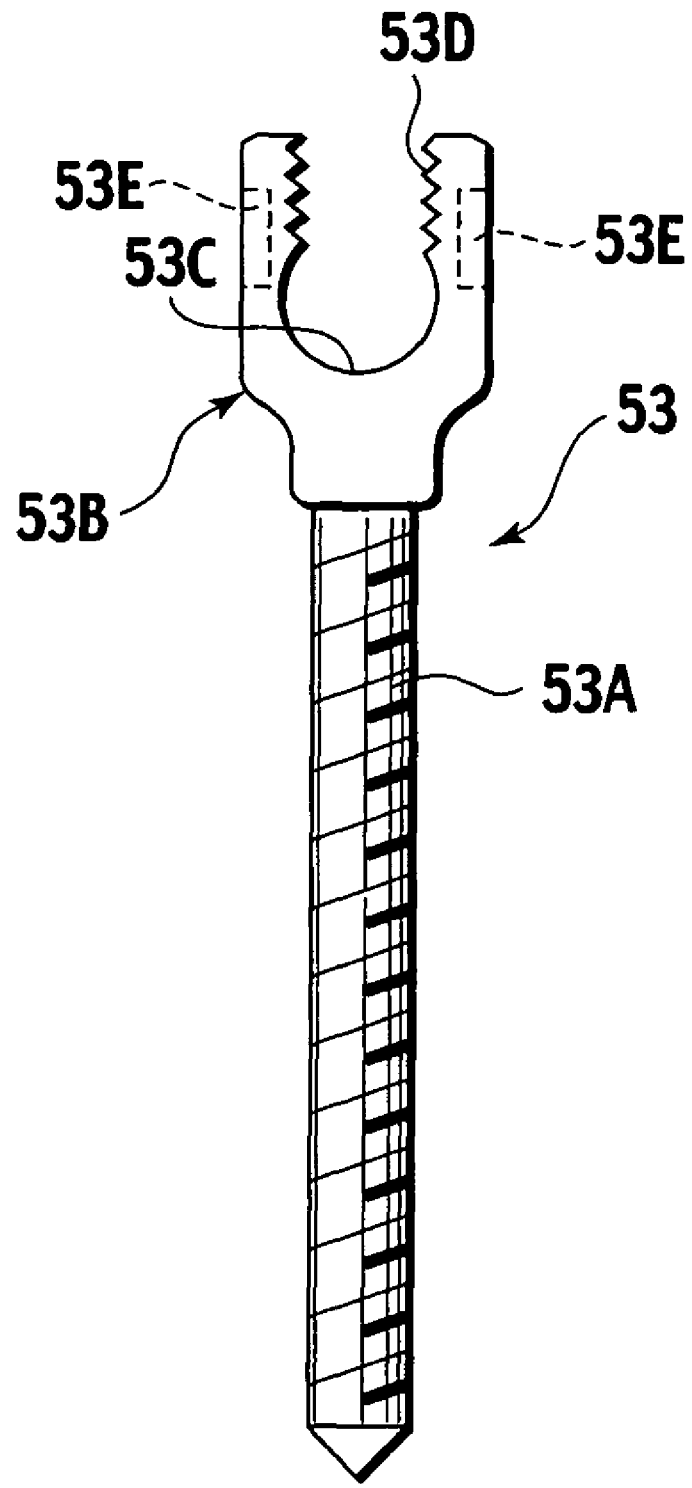
FIG. 5 is a front view of a screw employed in a second embodiment of the present invention.

As shown in FIG. 5, the screw 53 has a thread portion 53A, a head portion 53B, an engaging groove 53C, a female thread portion 53D and engaging holes 53E, 53E. The thread portion 53A to be screwed into the vertebral body is formed at a lower part of the screw 53. The square head portion 53B is formed at an upper part of the screw 53. The engaging groove 53C is formed at a center part of the head portion 53B. The rod 55 passes through a lower portion of the engaging groove 53C. The female thread portion 53D is formed on an upper part of an inner surface of the engaging groove 53C. A male thread portion (not shown) formed on an outer surface of the detent pin 57 is screwed into the female thread portion 53D. The engaging holes 53E, 53E are formed on an outer surface of the head portion 53B so as to be opposed to each other.

Figure 6:
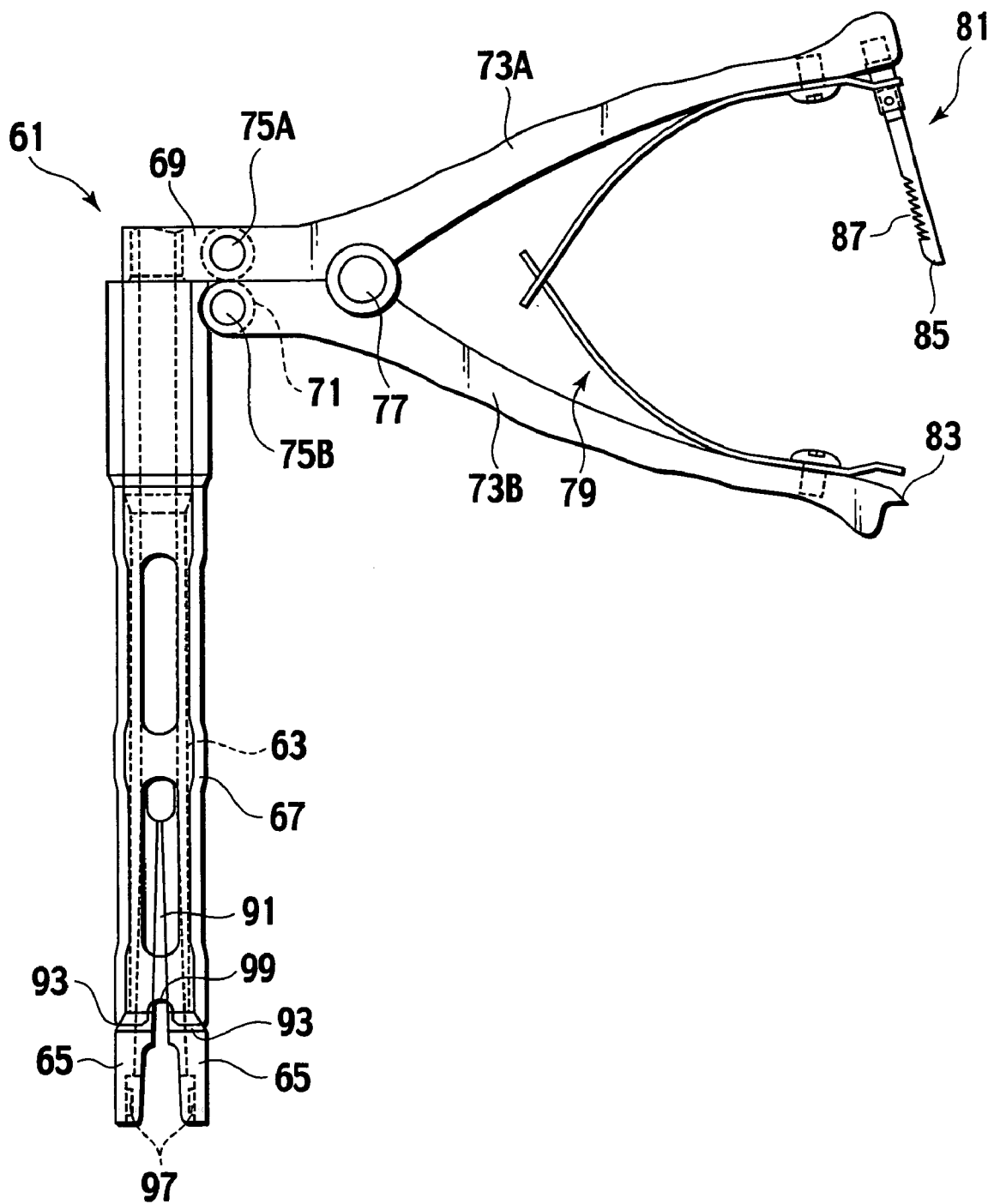
FIG. 6 is a front view of an auxiliary instrument for fixing a rod according to the second embodiment of the present invention.

As shown in FIG. 6, an auxiliary instrument for fixing a rod 61 comprises an inner cylinder 63, claw portions 65, 65, an outer cylinder 67, a first bracket 69, a second bracket 71, levers 73A, 73B, hinge pins 75A, 75B, a pivot 77, a biasing means 79 and a locking means 81.

The inner cylinder 63 branches in two directions as gently inclining outward from the vicinity of a center portion thereof. The inner cylinder 63 further has the claw portions 65, 65 at distal ends of branch parts thereof (a lower end of the inner cylinder 63). The head portion 53B of the screw 53 is sandwiched between the claw portions 65, 65. The outer cylinder 67 is arranged concentrically with the inner cylinder 63 and shorter than the inner cylinder 63. The outer cylinder 67 further is able to move along an axial direction of the inner cylinder 63. If the outer cylinder 67 moves down relative to the inner cylinder 63, the claw portions 65, 65 approach each other as guided by an inner circumference surface of the outer cylinder 67. The first bracket 69 is integrally mounted on an upper end portion of the inner cylinder 63 projecting upward from an upper end face of the outer cylinder 67. The second bracket 71 is integrally mounted on an upper end portion of the outer cylinder 67.

The levers 73A, 73B are employed to move the outer cylinder 67 along the axial direction of the inner cylinder 63. The levers 73A, 73B are connected to the first bracket 69 and the second bracket 71 via the hinge pins 75A, 75B, respectively.

More specifically, base end portions of the levers 73A, 73B are supported to the first bracket 69 and the second bracket 71 via the hinge pins 75A, 75B, respectively so that the levers 73A, 73B may pivot. The levers 73A, 73B are further connected each other via the pivot 77 so as to be able to swing at a position close to the end portions thereof.

The biasing means 79 is a leaf spring for biasing the levers 73A, 73B so as to bring the base end portions of the levers 73A, 73B close to each other. The biasing means 79 is mounted between the levers 73A, 73B. The biasing means 79 may be a means for biasing the lever 73A, 73B so as to bring the base end portions of the levers 73A, 73B close to each other without being limited to the leaf spring.

The locking means 81 is a means for holding a status where the base end portions of the levers 73A, 73B separates from each other against biasing force of the biasing means 79. The locking means 81 is mounted to free end portions of the levers 73A, 73B. The locking means 81 has a catching claw 83, a hold lever 85 and a caught portion 87. The catching claw 83 is mounted to the free end portion of the lever 73B. The hold lever 85 is mounted to the free end portion of the lever 73A and has the caught portion 87 to which the catching claw 83 is engaged.

Figure 7:
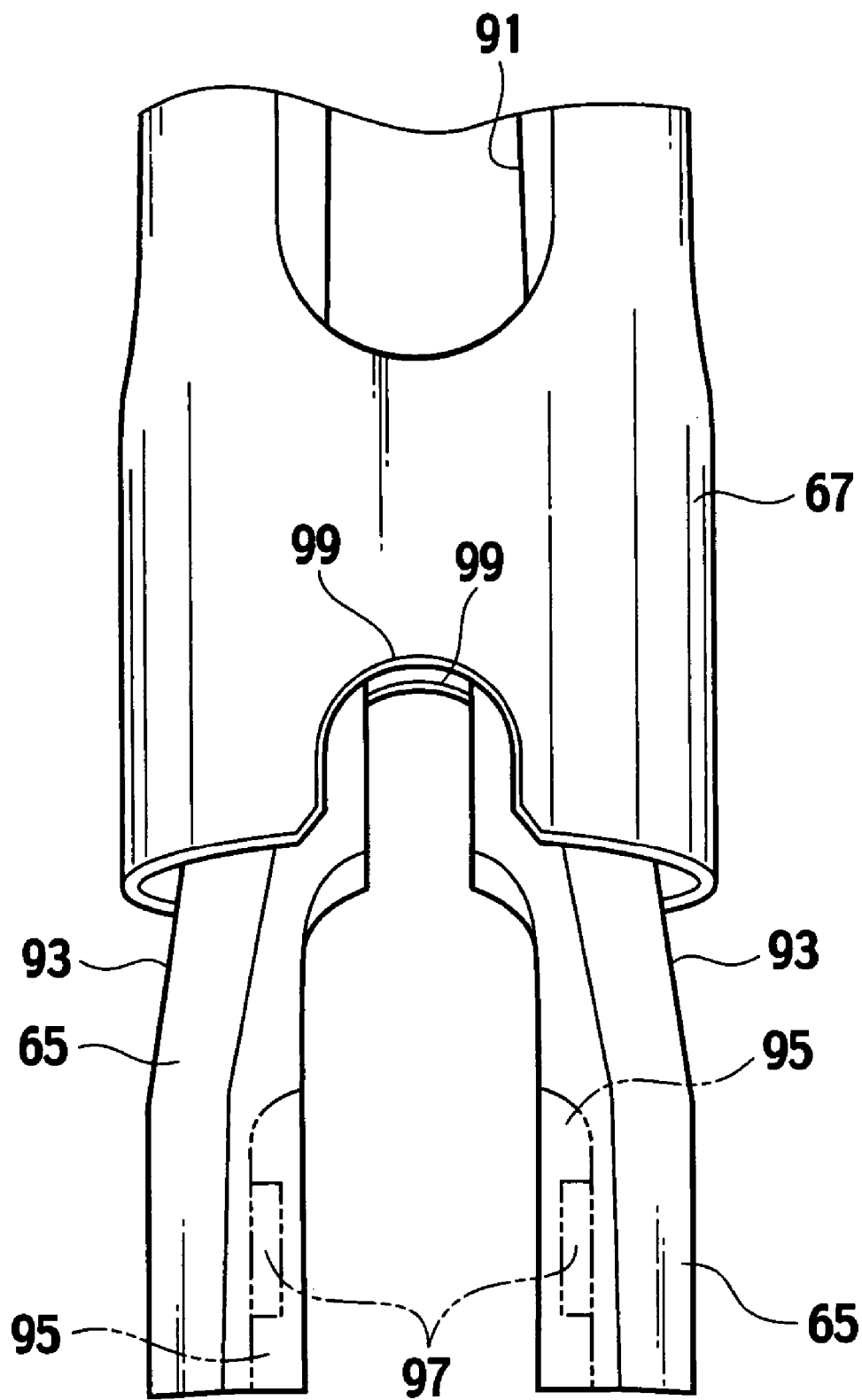
FIG. 7 is an enlarged perspective view of a lower portion of the auxiliary instrument for fixing a rod according to the second embodiment of the present invention.

Structure of a lower end portion of the inner cylinder 63 will be described in detail below. As shown in FIG. 7, in a situation where the auxiliary instrument 61 is unemployed, the inner cylinder 63 has a part projecting from a lower end face of the outer cylinder 67 at the lower end portion thereof. The claw portions 65, 65 are formed at the projecting part. A slit 91 is formed in the vicinity of the center portion of the inner cylinder 63 so as to divide the lower end portion of the inner cylinder 63 into two parts. Taper faces 93, 93 are formed on an outer circumference surface of the claw portions 65, 65 so as to gently incline outward. If the outer cylinder 67 moves down relative to the inner cylinder 63, the taper faces 93, 93 are pressed inward by the inner circumference surface of the outer cylinder 67.

Figure 9:
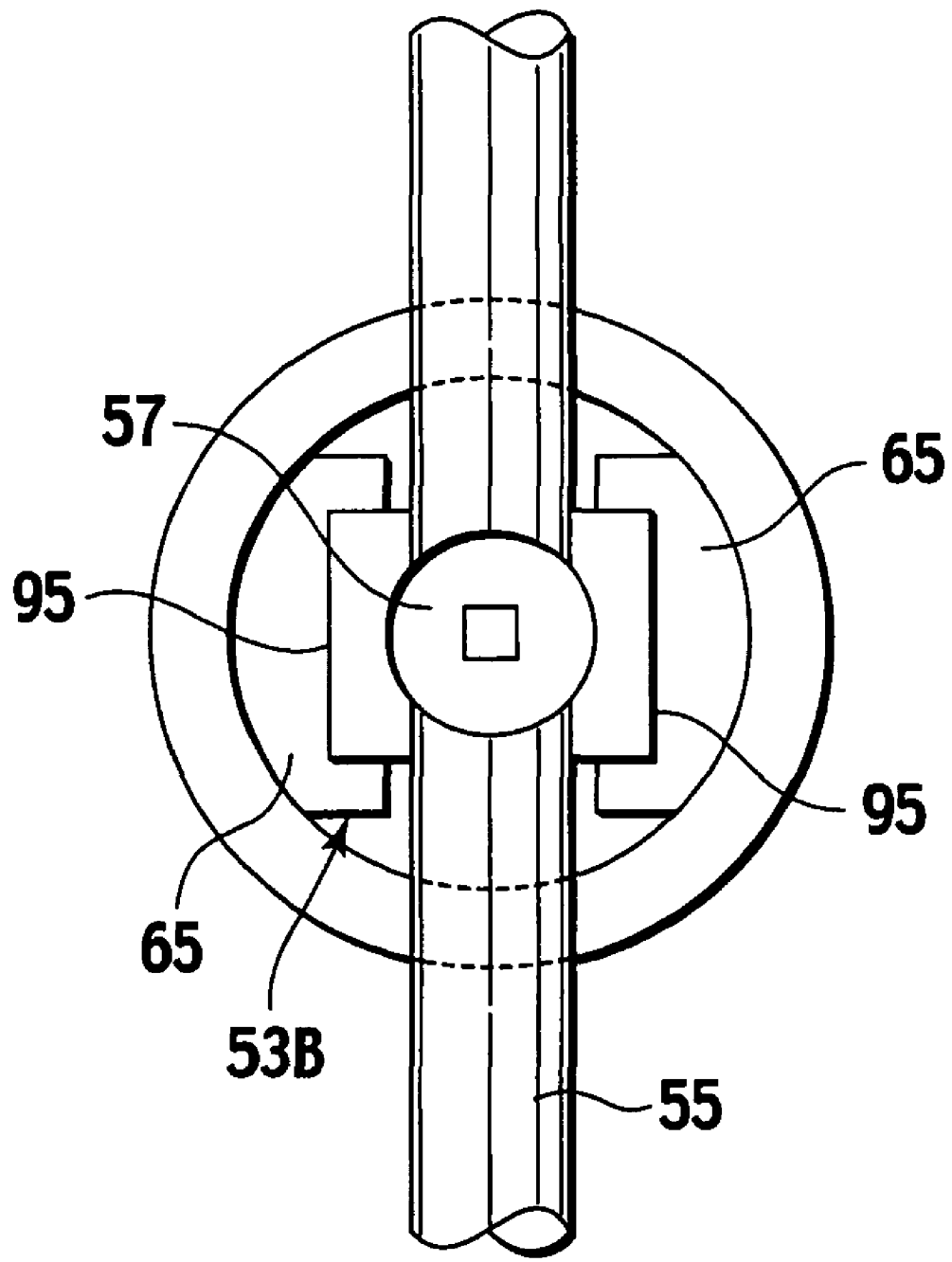
FIG. 9 is a cross-section view of the auxiliary instrument for fixing a rod along the line IX-IX in FIG. 8A.

Grooves 95, 95 are formed on inner surfaces of the claw portions 65, 65 so as to each be substantially shaped like a letter U in the cross-section view thereof and be fitted into a shape of a rising portion in the head portion 53B of the screw 53 (see FIG. 9). Engaging pins 97, 97 are provided in a protruding condition on inner surfaces of the grooves 95, 95. When the claw portions 65, 65 approach each other by moving the outer cylinder 67 down relative to the inner cylinder 63, the engaging pins 97, 97 are inserted into the engaged holes 53E, 53E formed on the head portion 53B of the screw 53. Rod holding portions 99, 99 are formed at a center area of the lower end portion of the outer cylinder 67 so as to be substantially shaped like a half circular arc. From above, the rod holding portions 99, 99 hold down the rod 55 which passes through the lower portion of the engaging groove 53C of the screw 53.

A work for fixing the rod 55 to the screw 53 by means of the auxiliary instrument 61 will be described in detail below. Firstly, the rod 55 passes through the lower portion of the engaging groove 53C formed on the head portion 53B of the screw 53. Secondly, a pair of the rising portions in the head portion 53B of the screw 53 are inserted into the grooves 95, 95 of the auxiliary instrument 61. Thirdly, the engaging pins 97, 97 of the auxiliary instrument 61 are inserted into the engaging holes 53E, 53E of the screw 53 by operating the levers 73A, 73B (see FIG. 8A).

The operation of the levers 73A, 73B will be described in detail below. An operator holds the levers 73A, 73B in his/her one hand to bring the free end portions of the levers 73A, 73B close to each other against biasing force of the biasing means 79, which allows the base end portions of the levers 73A, 73B to separate from each other.

Clearances are formed between the inner cylinder 63 and the outer cylinder 67, between the lever 73A and the hinge pin 75A, between the lever 73B and the hinge pin 75B, between the lever 73A and the pivot 77 and between the lever 73B and the pivot 77. A locus error, which is generated between arc movements of the base end portions of the levers 73A, 73B and line movements of the inner cylinder 63 and the outer cylinder 67 when the base end portions of the levers 73A, 73B separate from each other, is absorbed by these clearances.

When the base end portion of the levers 73A, 73B separate from each other, the taper faces 93, 93 of the claw portions 65, 65 are pressed inward by the inner circumference surface of the outer cylinder 67, which allows the engaging pins 97, 97 to be slightly inserted into the engaging holes 53E, 53E. In a case where the engaging pins 97, 97 are not inserted into the engaging holes 53E, 53E, the operator moves the inner cylinder 63 relative to the head portion 53B of the screw 53 upward or downward by operating the levers 73A, 73B, which allows the engaging pins 97, 97 to be slightly inserted into the engaging holes 53E, 53E.

When the operator further holds the levers 73A, 73B tightly in his/her one hand, the outer cylinder 67 moves downward relative to the inner cylinder 63, which allows the rod holding portions 99, 99 to hold the rod 55 down from above in a situation where the engaging pins 97, 97 are engaged into the engaging holes 53E, 53E. Then, a situation where the rod holding portions 99, 99 presses the rod 55 toward a bottom portion of the engaging groove 53C is held by engaging the catching portion 83 to the caught portion 87 of the hold lever 85 in the locking means 81 (see FIG. 8B).

Reactive force, which is generated when the rod 55 is pressed toward the bottom portion of the engaging groove 53C, is transmitted to the inner cylinder 63 via the outer cylinder 67, the lever 73A, the pivot 77 and lever 73B. However, an engagement of the engaging pins 97, 97 and the engaging holes 53E, 53E prevents the screw 53 from pulling out the vertebra body. Therefore, the rod 55 is steadily pressed toward the bottom portion of the engaging groove 53C by the rod holding portions 99, 99.

Figure 10B:
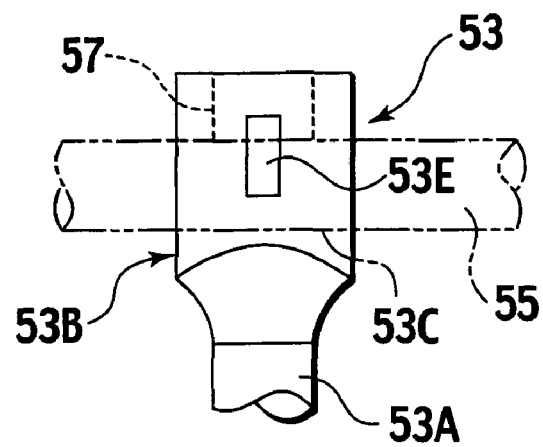
FIG. 10B is a side view of a main portion of the bone connector in the state of fixing the rod to the screw.
Figure 10A:
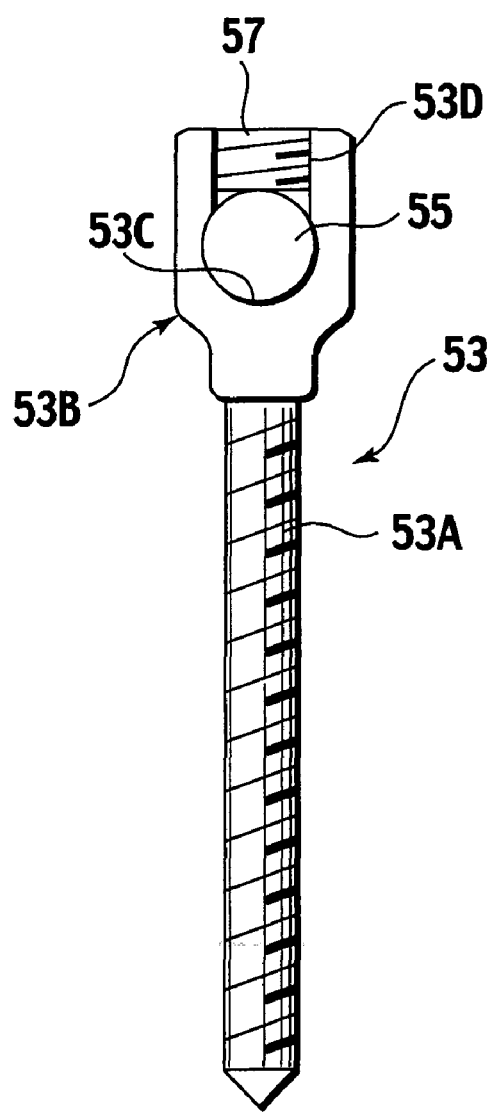
FIG. 10A is a front view of a bone connector in a state of fixing a rod to the screw.
Figure 10C:
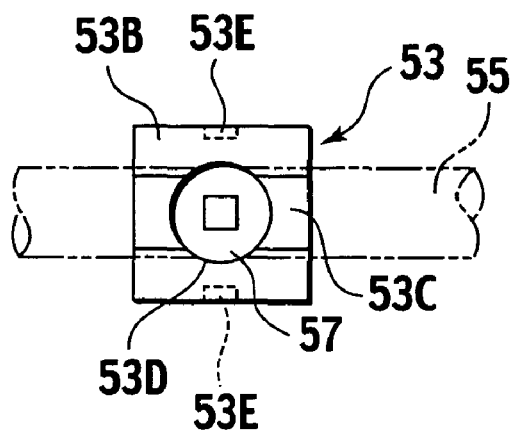
FIG. 10C is a plan view of the main portion of the bone connector in the state of fixing the rod to the screw.

Fourthly, when the detent pin 57 is dropped from an opening surface of the upper portion of the inner cylinder 63, the detent pin 57 is guided by an inner circumference surface of the inner cylinder 63 and then placed on an upper surface of the engaging groove 53C. Finally, a rotating tool 100 is inserted from the opening surface of the upper portion of the inner cylinder 63 and a lower end portion of the tool 100 is engaged to a polygonal tool engaging hole formed on an upper surface of the detent pin 57. Then, the operator holds a handle 100A of the tool 100 in his/her other hand and then screw the male thread portion of the detent pin 57 into the female thread portion 53D of the engaging groove 53C by rotating the tool 100. Thereby, the detent pin 57 presses the rod 55 toward the bottom portion of the engaging groove 53C (see FIGS. 10A to 10C).

The auxiliary instrument 61 has the following features in addition to the features of the auxiliary instrument 11.

Structure of the auxiliary instrument 61 is much simpler than that of the auxiliary instrument 11 because the auxiliary instrument 61 comprises the inner cylinder 63, the claw portions 65, 65, the outer cylinder 67, the first bracket 69, the second bracket 71, the levers 73A, 73B, the hinge pins 75A, 75B, the pivot 77, the biasing means 79 and the locking means 81.

The engaging pins 97, 97 are easily inserted into the engaging holes 53E, 53E because each of the rising portions in the head portion 53B of the screw 53 is restrained from three directions by the groove 95 of the claw portion 65.

The rod 55 is steadily fixed to the screw 53 by the detent pin 57 because the rod holding portions 99, 99 press the rod 55 toward the bottom portion of the engaging groove 53C.

In the auxiliary instrument 11, it is necessary for an operator who holds the lever 31 in his/her one hand and the rotating tool in his/her other hand to operate the rotating tool in a narrow space, because the rotating tool is arranged in substantially parallel to the lever 31. Therefore, an operationality of the rotating tool is bad. On the other hand, in the auxiliary instrument 61, it is necessary for an operator who holds the levers 73A, 73B in his/her one hand and the rotating tool 100 in his/her other hand to operate the rotating tool in a large space, because the rotating tool 100 is arranged in substantially perpendicular to the levers 73A, 73B. Therefore, an operationality of the rotating tool 100 is improved in comparison with the auxiliary instrument 11.

In the auxiliary instrument 11, when an operator holds the lever 31 in his/her one hand and the rotating tool in his/her other hand, the screw 3 may rotate with the rotating tool because the rotating tool is arranged in substantially parallel to the lever 31. On the other hand, in the auxiliary instrument 61, when an operator holds the levers 73A, 73B in his/her one hand and the rotating tool 100 in his/her other hand, the screw 53 may not rotate with the rotating tool 100 against rotation force of the rotating tool 100 to be easily pressed toward the vertebra body because the rotating tool 100 is arranged in substantially perpendicular to the levers 73A, 73B. Therefore, the auxiliary instrument 61 prevents the screw from rotating with the rotating tool in comparison with the auxiliary instrument 11.

In the auxiliary instrument 11, it is possible to hurt an incision part of a patient because the second links 23, 23 moves in a perpendicular direction relative to the axial direction of the rod 5. On the other hand, in the auxiliary instrument 61, the auxiliary instrument 61 can reduce volume occupied by a member inserted into the incision part and prevent the incision part from being hurt because there is not any link mechanism in the auxiliary instrument 61.

What is claimed is:

1. An auxiliary instrument for fixing a rod, the auxiliary instrument placing a detent pin employed to fix the rod to a screw on a head portion of the screw, the auxiliary instrument comprising:
    an inner cylinder member having a plurality of claw portions at a first end portion thereof and an opening employed to introduce the detent pin into an interior thereof at a second end portion thereof, the inner cylinder member further having a first bracket disposed at the second end portion thereof such that the first bracket projects from the inner cylinder member in a direction generally perpendicular to a longitudinal axial direction of the inner cylinder member;
    an outer cylinder member arranged to surround the inner cylinder member and having a claw pressing portion at a first end portion thereof, the outer cylinder member further having a second bracket at a second end portion thereof such that the second bracket projects from the outer cylinder member in generally a same direction as the first bracket;
    a first lever rotatably connected to the first bracket of the inner cylinder member such that the first lever is extended from the first bracket; and
    a second lever rotatably connected to the first lever and the second bracket of the outer cylinder member such that the second lever is extended from the second bracket,
    wherein the claw portions are pressed inward by the claw pressing portion to hold the head portion of the screw when the first lever and the second lever are operated.

2. The auxiliary instrument for fixing a rod according to claim 1, wherein the claw portions approach one another as being guided by the claw pressing portion formed on an inner circumference surface of the outer cylinder member when the outer cylinder member moves downward relative to the inner cylinder member.

3. The auxiliary instrument for fixing a rod according to claim 2, wherein the inner cylinder member branches in two directions tapering outwardly from the vicinity of a center portion to the first end portion thereof.

4. The auxiliary instrument for fixing a rod according to claim 3, wherein each of the claw portions has a groove configured to restrain the head portion of the screw in three directions.

5. The auxiliary instrument for fixing a rod according to claim 3, wherein the outer cylinder member has a rod holding portion configured to press the rod toward the head portion of the screw at the first end thereof.

6. The auxiliary instrument for fixing a rod according to claim 4, wherein each groove has an engaging pin to be engaged into an engaging hole formed on the head portion of the screw.

7. The auxiliary instrument for fixing a rod according to claim 1, further comprising:
    a biasing member mounted between the first lever and the second lever and configured to bring a base end portion of the first lever close to a base end portion of the second lever.

8. The auxiliary instrument for fixing a rod according to claim 7, further comprising:
    a locking member mounted to a free end portion of the first lever and configured to engage a free end portion of the second lever and configured to hold the base end portions in a manner separated from each other against a biasing force of the biasing member.

9. The auxiliary instrument for fixing a rod according to claim 1, wherein the inner cylinder member is configured to receive a rotating tool.

10. The auxiliary instrument for fixing a rod according to claim 9, wherein when the rotating tool is inserted in the inner cylinder member, the rotating tool is disposed perpendicular to the first lever and the second lever.

11. The auxiliary instrument for fixing a rod according to claim 1, wherein the first lever is connected to the first bracket through a hinge pin.

12. The auxiliary instrument for fixing a rod according to claim 1, wherein the second lever is connected to the second bracket through a hinge pin.

13. The auxiliary instrument for fixing a rod according to claim 1, wherein the claw portions are configured to grasp the head portion of the screw on sides thereof.

14. An auxiliary instrument for fixing a rod, the auxiliary instrument placing a detent pin employed to fix the rod to a screw on a head portion of the screw, the auxiliary instrument comprising:
    an inner cylinder member having a plurality of claw portions at a first end portion thereof and an opening employed to introduce the detent pin into an interior thereof at a second end portion thereof, the inner cylinder member further having a first bracket disposed at the second end portion thereof;

an outer cylinder member arranged to surround the inner cylinder member and having a claw pressing portion at a first end portion thereof, the outer cylinder member further having a second bracket disposed at a second end portion thereof;

a first lever pivotally connected to the first bracket of the inner cylinder member through a hinge pin; and a second lever pivotally connected to the second bracket of the outer cylinder member through a hinge pin and pivotally connected to the first lever through a pivot, wherein the claw portions are pressed inward by the claw pressing portion to hold the head portion of the screw when the first lever and the second lever are operated.

15. The An auxiliary instrument for fixing a rod according to claim 14, wherein the inner cylinder member is configured to receive a rotating tool.

16. The An auxiliary instrument for fixing a rod according to claim 15, wherein when the rotating tool is inserted in the inner cylinder member, the rotating tool is disposed perpendicular to the first lever and the second lever.

17. An auxiliary instrument for fixing a rod, the auxiliary instrument placing a detent pin employed to fix the rod to a screw on a head portion of the screw, the auxiliary instrument comprising:

an inner cylinder member having a plurality of claw portions at a first end portion thereof and an opening employed to introduce the detent pin into an interior thereof at a second end portion thereof, the inner cylinder member further having a first bracket disposed at the second end portion thereof;

an outer cylinder member arranged to surround the inner cylinder member and having a claw pressing portion at a first end portion thereof, the outer cylinder member further having a second bracket disposed at a second end portion thereof;

a first lever rotatably connected to the first bracket of the inner cylinder member through a hinge pin and crossing a longitudinal direction of the inner cylinder member, the first lever configured to pivot in a plane including the longitudinal direction of the inner cylinder member; and a second lever rotatably connected to the first lever and the second bracket of the outer cylinder member through a hinge pin and crossing a longitudinal direction of the outer cylinder member, the second lever configured to pivot in a plane including the longitudinal direction of the outer cylinder member, wherein the claw portions are pressed inward by the claw pressing portion to hold the head portion of the screw when the first lever and the second lever are operated.

18. The An auxiliary instrument for fixing a rod according to claim 17, wherein the inner cylinder member is configured to receive a rotating tool.

19. The An auxiliary instrument for fixing a rod according to claim 18, wherein when the rotating tool is inserted in the inner cylinder member, the rotating tool is disposed perpendicular to the first lever and the second lever.

20. An auxiliary instrument for fixing a rod, the auxiliary instrument placing a detent pin employed to fix the rod to a screw on a head portion of the screw, the auxiliary instrument comprising:

an inner cylinder member having a plurality of claw portions at a first end portion and an opening employed to introduce the detent pin into an interior thereof at a second end portion thereof, the inner cylinder member further having a first bracket disposed at the second end portion thereof such that the first bracket projects in a direction generally perpendicular to a longitudinal axis of the inner cylinder member;

an outer cylinder member arranged to surround the inner cylinder member and having a claw pressing portion at a first end portion thereof, the outer cylinder member further having a second bracket disposed at a second end portion thereof such that the second bracket projects in generally a same direction as the first bracket;

a first lever rotatably connected to the first bracket of the inner cylinder member and arranged generally perpendicular to a longitudinal direction of the inner cylinder member and movable along a longitudinal axial direction of the inner cylinder member; and a second lever rotatably connected to the first lever and the second bracket of the outer cylinder member and arranged such that the second lever is pivotally moved on a same plane as the movement of the first lever along a longitudinal axial direction of the outer cylinder member, wherein the claw portions are pressed inward by the claw pressing portion to hold the head portion of the screw when the first lever and the second lever are operated.

* * * * *

UNITED STATES PATENT AND TRADEMARK OFFICE
CERTIFICATE OF CORRECTION

| | | |
|---|---|---|
| PATENT NO. | : 7,909,835 B2 | Page 1 of 1 |
| APPLICATION NO. | : 11/073590 | |
| DATED | : March 22, 2011 | |
| INVENTOR(S) | : K. Oribe et al. | |

It is certified that error appears in the above-identified patent and that said Letters Patent is hereby corrected as shown below:

At column 9, line 14 (claim 15, line 1) of the printed patent, please delete "An" between "The" and "auxiliary".

At column 9, line 17 (claim 16, line 1) of the printed patent, please delete "An" between "The" and "auxiliary".

At column 10, line 4 (claim 18, line 1) of the printed patent, please delete "An" between "The" and "auxiliary".

At column 10, line 7 (claim 19, line 1) of the printed patent, please delete "An" between "The" and "auxiliary".

Signed and Sealed this
Twenty-fifth Day of October, 2011

David J. Kappos
*Director of the United States Patent and Trademark Office*